Figure 1:
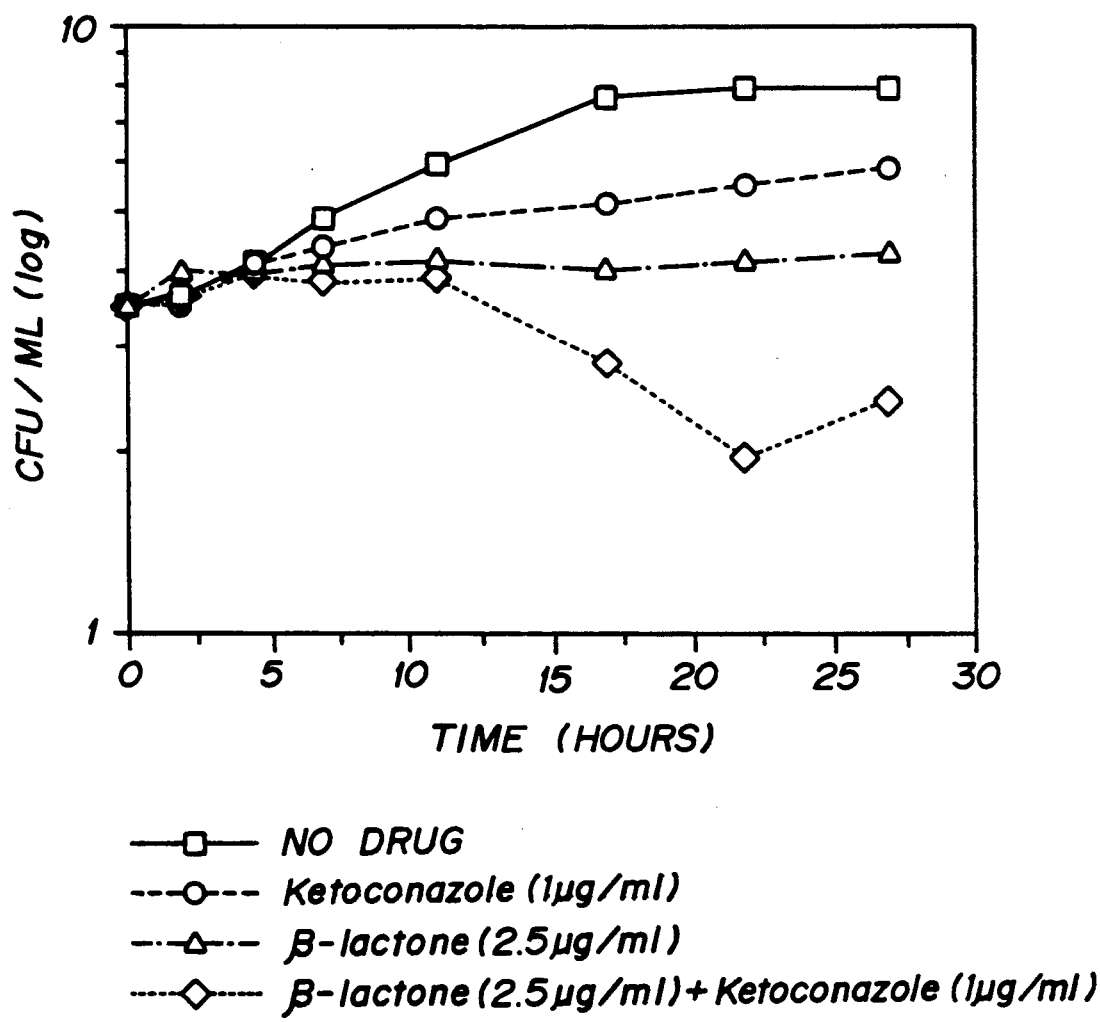

United States Patent [19]

Onishi

[11] Patent Number: 4,988,697

[45] Date of Patent: Jan. 29, 1991

[54] FUNGICIDAL COMPOSITIONS AND METHOD

[75] Inventor: Janet C. Onishi, Mountainside, N.J.

[73] Assignee: Merck & Co., Inc., Rahway, N.J.

[21] Appl. No.: 386,320

[22] Filed: Jul. 28, 1989

[51] Int. Cl.$^5$ .................. A61K 31/495; A61K 31/50; A61K 31/41; A61K 31/335; A61K 31/415
[52] U.S. Cl. .................................... 514/252; 514/383; 514/399; 514/449
[58] Field of Search ............... 514/252, 210, 383, 399, 514/449

[56] References Cited

U.S. PATENT DOCUMENTS 4,782,059 11/1988 Gadebusch et al. ................ 514/252

FOREIGN PATENT DOCUMENTS 0234752 9/1987 European Pat. Off. .

OTHER PUBLICATIONS

D. C. Aldridge, D. Giles, W. B. Turner, Antibiotic 1233A: A Fungal-Lactone, J. Chem. Soc. (C), 1971, pp. 3888-3891.
Drugs of Today, vol. 20, No. 7, 1984, pp. 325-349.

Primary Examiner—Douglas W. Robinson
Assistant Examiner—Raymond J. Henley, III
Attorney, Agent, or Firm—Alice O. Robertson; Charles M. Caruso

[57] ABSTRACT

Novel fungicidal compositions comprising a 14α-methyldemethylase inhibiting azole compound and a β-lactone compound and a method for controlling mycotic infections is disclosed.

15 Claims, 2 Drawing Sheets

FUNGICIDAL COMPOSITIONS AND METHOD

BACKGROUND OF THE INVENTION

Fungal diseases or mycoses may be superficial, affecting primarily skin, hair and mucous membrane, or may be deep or systemic, affecting lungs and other internal organs. The superficial mycotic infections which are caused by organisms referred to as dermatophytes are generally considered more annoying than serious. The deep or systemic mycotic infections which are caused generally by different organisms are quite serious, frequently resulting in death.

Antifungal agents considered with specific reference to deep or systemic fungal infections caused by organisms such as Candida species, Cryptococcus neoformans, Histoplasma capsulatum and the like are found for the most part to be fungistatic, i.e., merely inhibit the growth of the fungal organism without effecting a kill. A few fungicidal agents are known. Amphotericin B and other polyenes are known to damage membranes that contain ergosterol and therefore are effectively fungicidal. However, their use is normally precluded because of a number of severe side effects. Other possibly fungicidal drugs, e.g. 5-fluorocytosine, have side effects or may be limited by the scope of their spectrum. 5-Fluorocytosine is further limited by the ease with which an organism develops resistance to it. In the search for antifungal drugs for treating systemic infections, it is desirable to find a drug or a combination of drugs which is effective at low concentration levels thereby minimizing side effects. It is particularly desirable to find a drug or a combination of drugs in which the resultant drug is fungicidal.

STATEMENT OF THE INVENTION

The present invention concerns an improved method for the treatment of deep or system mycotic infections made possible by the discovery than when certain fungistatic agents namely, a 14 α-methyldemethylase inhibiting azole compound and a β-lactone compound, are employed in combination, a synergistic antifungal combination is obtained. It has been found further than certain combinations are able further to cause irreversible damage to the fungi resulting in a killing or cidal effect on the fungi. The β-lactone compound as a component is especially desirable because the high effectiveness of the β-lactone compound itself is such as to render the combination effective at very lose doses. The invention also concerns fungicidal compositions which are suitable for use in the treatment of system mycotic infections.

DESCRIPTION OF THE INVENTION

The fungicidal composition of the present invention comprises a β-lactone compound and a 14 α-methyldemethylase inhibiting compound.

The β-lactone component is a compound having the formula

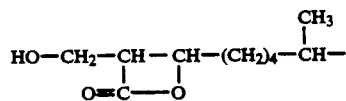

-continued

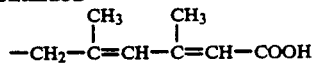

or a pharmaceutically acceptable salt thereof. The compound is named 11-(3-hydroxymethyl-4-oxo-2-oxetanyl)-7-methyl-2,4-undecadienoic acid and may be produced by fungi; it is also known as Antibiotic 1233A reported by Aldridge et al, Chem. Comm., 1970, p. 639 and in J. Chem. Soc (c), 1971, pp. 3888-3890 (1972). The antifungal properties of the compound against fungi such as Trichophyton sp., Cryptococcus sp., Hormodendrum sp., Geotrichum sp., and Candida sp. are disclosed in the U.S. Ser. No. 825,496 filed Feb. 3, 1986, now abandoned; published by EPO under 0234752, Sept. 2, 1987. The teachings of the foregoing are incorporated herein by reference.

The pharmaceutically acceptable salts of the β-lactone component of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The 14-α-methyldemethylase inhibiting azole compounds are generally well-known for treating human mycotic infections, and the more important compounds imidazoles and triazoles. Many of these compounds are in use clinically as fungistats or are being developed for such purpose. The generic drug names for those compounds already developed or being developed have the suffix "conazole." In subsequent discussions, the compounds will sometimes will be referred to as "conazole compounds," even though some may not have a generic name. The foremost compound is ketoconazole which is cis-1-acetyl- 4-[4-[[2-(2,4-dichlorophenyl)-2-(1H-imidazole-1-ylmethyl)-1,3-dioxolan-4-yl]methoxy]-phenyl]piperazine. Other fungistatic conazole compounds which are 14 α-methyldemethylase inhibitors and which are either in clinical use or in development include fluconazole, α-(2,4-difluorophenyl)-α-(1H-1,2,4-triazol-a-ylmethyl)-1H-1,2,4,-triazole-1-ethanol; miconazole, 1-[2,4-dichloro-β-(2,4-dichlorobenzyloxy) phenethyl]imidazole as nitrate; econazole, 1-[2-(2,4-dichlorophenyl)-2-(4-chlorobenzyloxy) ethyl]imidazole; isoconazole, 1-[2,4-dichloro-β(2,6- dichlorobenzyloxy)phenethyl]imidazole as nitrate; terconazole, cis-1,4,2-(2,4-dichlorophenyl)-2-(1-ylmethyl)-1,3-dioxolan-4-yl-methoxy-phenyl-4-(methyl-ethyl)piperazine; tioconazole, 1-[2-[(2-choloro-3-thienyl)methoxy]-2-(2-choloro-3-thienyl)methoxy]-2-(2,4-dichlorophenyl) ethyl]-1H-imidazole;bifonazole, 1-[(4-biphenyl)phenyl-methyl]-1H-imidazole. Still other azoles include ICI-153066 (ICI Pharmaceutical Division), [(R,S)-1-(2,4-dichlorophenyl)-1-(4- fluorophenyl)-2-(1,2,4-triazol-1-yl)ethanol]; Bay-n-7133 (Bayer AG, West Germany), 1-(4-chlorophenoxy)-3,3'-dimethyl-2-(1,2,4-triazol-1-yl)-methylbutan-2-ol; (E)-1-(5-chlorothien-2-yl)-2-(1H-imidazole-1-yl)ethanone-2, 6-dichlorophenylhydrazone hydrochloride; SM-4770 (Sumitomo Chemical Co., Ltd.), (R)-3-(n-butylthio)-2-(2,4-dichloro-phenyl)-1-(imidazole-1-yl)-2-propanol hydrochloride; oriconazole or itraconazole, (+)-cis-4-[4-[4-[[2-(2,4-dichlorophenyl)-2-(1H-1,2-4-triazol-1- ylmethyl)-1,3-dioxolan-4-yl]-methoxy] phenyl]-1-piperazinyl]phenyl]-2,4-dihydro-2-(1-methylpropyl)-3H-1,2,4-triazol-3-one; fenticonazole, α-(2,4-dichlorophenyl)-β,N-imidazolylethyl-4-phenyl-thiobenzylether nitrate; oxiconazole,(Z)-[2,4-dichloro-2-imidazole-1-yl)acetophenone]-0-(2,4-di-chlorobenzyl)oxime; omoconazole(E)-1-[2,4-chloro-β-[2-(p-chloro-phenoxy)ethoxy]-α-methylstyryl]imidazole ;aliconazole. Still other imidazole antifungal compounds which may be employed include methyl-4-[3-2-methyl-5-nitro-1H-imidazole-1-yl)propyl]piperazine, 5-nitro-(1-methylimidazolyl-t-butyl)(2-hydroxy-5-methoxyphenyl)carbinol, Z-1-[2-(2,4-dichlorophenyl)-3-methyl-1-pentenyl]-1H-imidazole hydrochloride, cis-3-(2-chloro-3-thienylmethyloxy)-2,3-dihydro-5-fluoro-2-(1-imidazolylmethyl)benzo[b]thiophene.

The azole compounds may have a basic nitrogen and therefore may be present as an acid addition salt. Pharmaceutically acceptable salts suitable as acid addition salts include those from acids such as hydrochloric, hydrobromic, hydroiodic, phosphoric, sulfuric, trifluoroacetic, trichloracetic, oxalic, maleic, pyruvic, malonic, succinic, citric, mandelic, benzoic, cinnamic, methanesulfonic, ethanesulfonic, trifluoromethanesulfonic and the like. Reference to conazole compounds is intended to embrace both forms.

Many of the conazole compounds are established antifungal compounds. Ketoconazole is one of the preferred antifungal compounds for its broad spectrum and substantial absence of side effects. The combination of ketoconazole and 11-(3-hydroxy-methyl-4-oxo-2-oxetanyl)-7-methyl-2,4-undecadienoic acid hereinafter ("β-lactone compound") represents a preferred embodiment of the present invention.

The synergistic antifungal and fungicidal combinations of the present invention are effective in the the treatment of mycotic infections caused by such fungal organisms as Candida species, for example, *C. albicans*, *C. tropicalis*, and *C. stellatoidea*.

The efficacy of the combination of the present invention in producing a synergistic antifungal as well as fungicidal effect may be seen in the in vitro interaction studies for the determination of activity and determination of viable cells. Synergistic antifungal properties have been demonstrated with ketoconazole and the β-lactone compound in tests against a representative fungal organism known to be the causative agent of mycotic infections, such as *Candida albicans*. Representative synergistic antifungal and fungicidal properties of combinations of the β-lactone compound and various conazole compounds are demonstrated against *Candida albicans* as seen in the following examples.

Minimum Inhibitory Concentration of β-Lactone Compound 11-(3-hydroxymethyl-4-oxo-2-oxetanyl)-7-methyl-2,4-undecadienoic acid (β-lactone compound), was solubilized in 100 percent dimethylsulfoxide (DMSO). Twofold dilutions were made with DMSO to obtain final drug concentrations in the broth dilution assay tubes ranging from 0.625 to 100 μg/ml.

The *Candida albicans*, MY 1055, yeast culture maintained in yeast nitrogen base/glucose (½ percent), YNB/G, was transferred to fresh medium and incubated 7 hours at 37° with shaking at 250 rpm. After incubation, each culture was diluted to $A_{600}=0.0004$ U/ml which was previously determined to be equal to 3000 cfu/ml (colony forming units per milliliter).

1 milliliter of YNB/G inoculated with yeast culture was added to sterile test tubes. The tubes were incubated at 250 rpm, 37° C. for 17 hr. The minimum inhibitory concentrations (MIC) was recorded as the lowest concentration of drug showing visible growth.

The minimum inhibitory concentration, against *Candida albicans* MY 1055, was determined to be a 2.5 μg/ml.

Minimum Fungicidal Concentration of β-Lactone Compound

In the manner above described for the determination of minimum inhibitory concentration, broth dilution assay tubes were prepared ranging from 0.625 to 100 μg/ml and 1 milliliter of YNB/G inoculated with *Candida albicans* MY 1055 sterile test tubes. The tubes were incubated at 250 rpm at 37° C. for 17 hours.

The minimum fungicidal concentration (MFC) was determined by serially diluting samples of MIC tubes in 0.9% saline. Aliquots were plated on Sabouraud dextrose agar. The plates were incubated at 37° for 48 hr. and the colonies counted. From the counts obtained, the number of cfu/ml in the undiluted drug-culture tube was calculated. The MFC is defined as the minimum amount of drug required to reduce the number of viable cells initially present in the drug-culture tubes greater than or equal to 95%. The MFC was 10 μg/ml.

Synergistic & Fungicidal Effect β-Lactone and Ketoconazole

Synergistic and fungicidal effects were determined by treating exponential phase *Candida albicans* cultures with β-Lactone at MIC and MFC levels and ketoconazole at 0.1 μg/ml or a 1 μg/ml alone or in combination. Exponential phase cultures were prepared by diluting an overnight culture 1:50 or 1:1000 in YNB/G. After incubating the diluted cells 7 or 17 hrs. at 37° C., the exponential phase cells were diluted in YNB/G to $A_{600}=0.0004$ u/ml to obtain 3000 cfu/ml.

10 microliters (μl) of β-lactone compound or ketoconazole prepared in DMSO was added to 1 ml of diluted exponential phase cells. The tubes were incubated at 37° C. at 250 rpm for 27 hours. Periodically, aliquots were diluted in 0.9% saline and plated on Sabouraud dextrose agar plates to determine the number of cfu/ml.

A. Synergistic Effect

The result for the β-lactone compound at minimum inhibitory concentration of 2.5 μg/ml with and without 1 μg/ml of ketoconazole are seen in Table 1 and FIG. 1.

TABLE 1

| | Fungal Growth (CFU/ML) | | | |
|---|---|---|---|---|
| Time (Hours) | No Drug | β-Lactone Compound (2.5 μg/ml) | Ketoconazole (1 μg/ml) | β-Lactone Compound (2.5 μg/ml) + Ketoconazole (1 μg/ml) |
| 0 | $2.95 \times 10^3$ | | $2.95 \times 10^3$ | |
| 2 | $3.85 \times 10^3$ | $3.85 \times 10^3$ | $5.1 \times 10^3$ | $9.20 \times 10^3$ |
| 4.5 | $1.30 \times 10^4$ | $8.80 \times 10^3$ | $1.09 \times 10^4$ | $8.50 \times 10^3$ |
| 7 | $6.65z10^4$ | $1.12 \times 10^4$ | $2.40 \times 10^4$ | $6.75 \times 10^3$ |
| 11 | $9.45 \times 10^5$ | $1.28 \times 10^4$ | $6.90 \times 10^4$ | $7.00 \times 10^3$ |
| 17 | $4.05 \times 10^7$ | $9.35 \times 10^3$ | $1.36 \times 10^5$ | $5.90 \times 10^2$ |
| 22 | $7.30 \times 10^7$ | $1.23 \times 10^4$ | $3.30 \times 10^5$ | $9.00.10^1$ |
| 27 | $7.00 \times 10^7$ | $1.80 \times 10^4$ | $7.20 \times 10^5$ | $2.50 \times 10^2$ |

The results show that after 17 hours, there is a definite synergistic effect of the combination of the β-lactone compound and ketoconazole.

B. Fungicidal Effect

Figure 2:
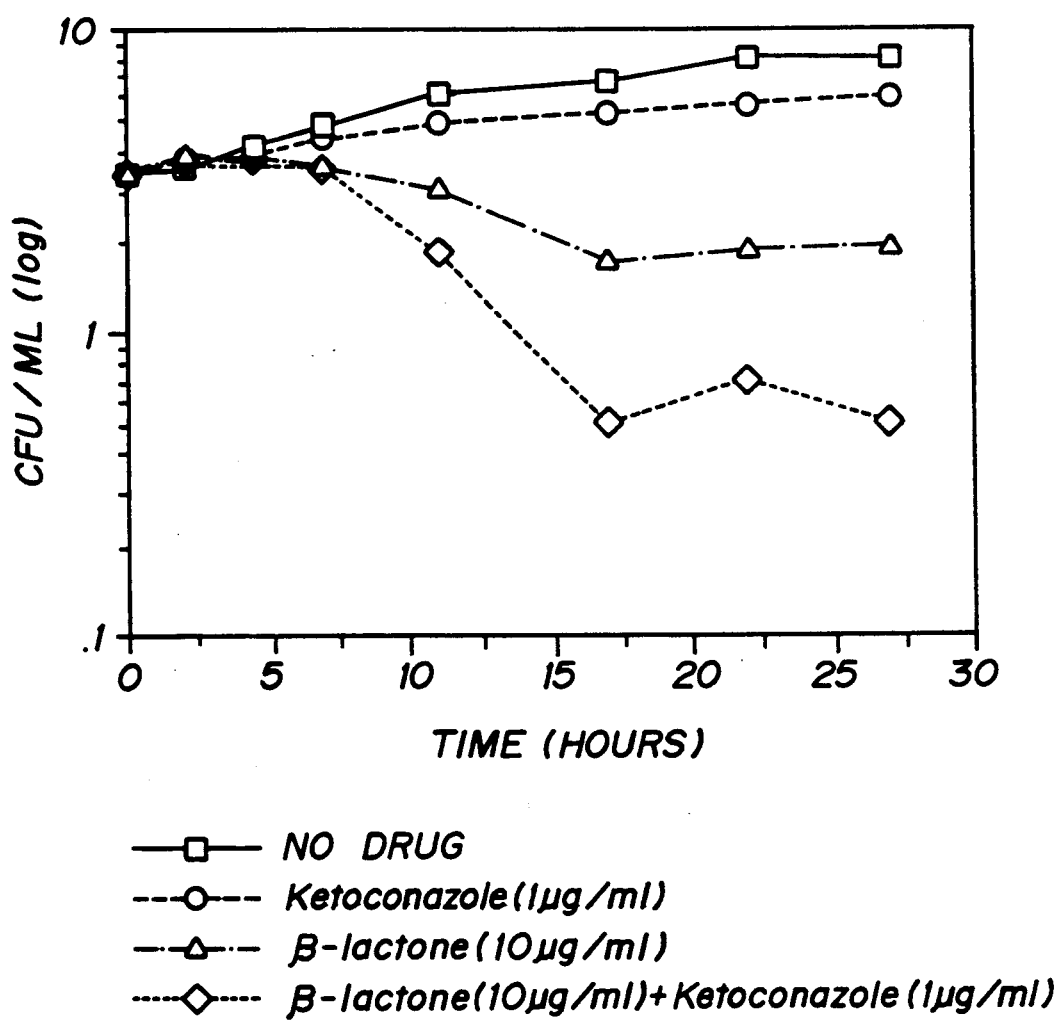

The results for the β-lactone compound at 4 times the minimum inhibitory concentration with and without 1 μg/ml of ketoconazole are seen in Table 2 and FIG. 2.

TABLE 2

Fungal Growth (CFU/ML)

| Time (Hours) | No Drug | β-Lactone Compound (10 μg/ml) | Keto-conazole (1 μg/ml) | β-Lactone Compound (10 μg/ml) + Ketoconazole (1 μg/ml) |
|---|---|---|---|---|
| 0 | $2.95 \times 10^3$ | | $2.95 \times 10^3$ | |
| 2 | $3.85 \times 10^3$ | $6.50 \times 10^3$ | $5.1 \times 10^3$ | $5.20 \times 10^3$ |
| 4.5 | $1.30 \times 10^4$ | $7.50 \times 10^3$ | $1.09 \times 10^4$ | $3.95 \times 10^3$ |
| 7 | $6.65 \times 10^4$ | $3.35 \times 10^3$ | $2.40 \times 10^4$ | $3.85 \times 10^3$ |
| 11 | $9.45 \times 10^5$ | $8.70 \times 10^2$ | $6.90 \times 10^4$ | $7.00 \times 10^1$ |
| 17 | $4.05 \times 10^7$ | $5.00 \times 10^1$ | $1.36 \times 10^5$ | 0 |
| 22 | $7.30 \times 10^7$ | $6.50 \times 10^1$ | $3.30 \times 10^5$ | 5 |
| 27 | $7.00 \times 10^7$ | $7.50 \times 10^1$ | $7.20 \times 10^5$ | 0 |

The results show that after 17 hours, complete kill of the microorganism is effected by the combination of the β-lactone at MFC (10 μg/ml) and ketoconazole at 1 μg/ml.

Synergistic Effect of β-Lactone Compound and Different Conazoles

The effectiveness of the combination of the β-lactone compound with various conazole compounds may be illustrated with ketoconazole, fluconazole and itraconazole.

The β-lactone compound and the following conazole compounds: cis-1-acetyl-4-[4-[[2-(2,4-dichlorophenyl)-2-1H-imidazole-1-ylmethyl)-1,3-dioxolan-4-yl]-methoxyl]phenyl]piperazine (ketoconazole), α-(2,4-difluorophenyl)-α-(1H-1,4-triazol-1-ylmethyl)1H-1,2-4-triazole-1-ethanol (fluconazole and cis-4-[4-[4-[[2-(2,4-dichlorophenyl)-2-(1H-1,2,4-triazole-1-ylmethyl)-1,3-dioxolan-4-yl]-methoxy] phenyl]-1-piperazinyl]phenyl-2,4-dihydro-2-(1-methylpropyl)-3H-1,2,4-triazol-3-one (itraconazole), were dissolved in DMSO and serially diluted in the manner previously described.

Assay tubes were prepared in a manner similar to that previously described and in operations carried out in a manner similar to that previously described, the effect of various conazole compounds on the MIC of the β-lactone compound were determined. The results are summarized in Table 3.

TABLE 3

Effect of Azole Antifungals on the MIC'S of the β-Lactone Compound Against *Candida albicans* MY 1055

| POTENTIA-TOR (μg/ml) | MIC'S OF β-LACTONE COMPOUND | | |
|---|---|---|---|
| | FLUCON-AZOLE | ITRACONAZOLE (μg/ml) | KETOCON-AZOLE |
| 0 | 2.5 | 2.5 | 2.5 |
| 0.3125 | 1.25 | 2.5 | 0.625 |
| 1.25 | 0.625 | 1.25 | 0.625 |
| 5.0 | 0.625 | 1.25 | 0.625 |

Synergistic Effect of β-Lactone Compound and Ketoconazole Against Fungal Panel In a manner similar to that above described for effect against *Candida albicans* the synergistic effect of the combination of the β-lactone compound and ketoconazole against a fungal panel was determined by plating on potato dextrose agar.

First the MIC for the β-lactone compound and the MIC for the ketoconazole were determined against an array of organisms. Thereafter, the effects on the MIC of adding 0.031, 0.125, 0.5 and 2 μg/ml of ketoconazole were determined. The results are seen in Table 4.

TABLE 4

Minimum Inhibitory Concentration (MIC)

| Organism | β-Lactone Compound in Presence of Ketoconazole μg/ml of Ketoconazole | | | | | Keto-conazole Alone μg/ml |
|---|---|---|---|---|---|---|
| | 0 | 0.031 | 0.123 | 0.5 | 2 | |
| *A. niger* | >50 | >50 | >50 | >50 | >50 | >2 |
| *C. miyabeamis* | 0.78 | 0.39 | 0.78 | 0.195 | N.G. | 2 |
| *F. oxysporium* | >50 | >50 | >50 | >50 | >50 | >2 |
| *U. zeae* | 3.125 | 3.125 | 0.78 | 0.19 | 0.19 | >2 |
| *C. neoformans* | 12.5 | 12.5 | 3.125 | 0.19 | 0.19 | >2 |
| *C. albicans* (Y1055) | 3.125 | 0.78 | 0.78 | 0.19 | 0.19 | >2 |
| *C. albicans* (Y1750) | 3.125 | 0.78 | 0.195 | 0.19 | 0.19 | >2 |

From the foregoing test results and from known dosage ranges of the "conazole compound" as applied to man, it is determined that generally from about 2.85 to about 4.75 mg/kg of body weight of the conazole compound and about 2.85 to about 4.75 mg/kg of body weight of the β-lactone compound is to be employed while considering patient's health, weight, age and other factors which influence response to a drug as well as the particular drug to be employed. These amounts when expressed as doses suitable for man are in the range of from about 200 to about 400 mg of each active ingredient given BID by oral or parenteral route.

According to the present invention, the synergistic antifungal or fungicidal composition may be formulated for injection and may be present in unit dosage form in ampoules or in multidose containers, if necessary, with an added preservative. The compositions may also take such forms as suspensions, solutions or emulsions in oily or aqueous vehicles, and may contain formulating agents such as suspending, stabilizing and/or dispersing agents. Alternatively, the active ingredients may be in powder form for reconstituting with a suitable vehicle prior to parenteral or oral administration.

The compounds also may be prepared in tablet or capsule form as well as in liquid form for oral administration. These also may be in unit dosage form.

For parenteral applications the drugs may be formulated in conventional parenteral solutions such as 0.85 percent sodium chloride or 5 percent dextrose in water, or other pharmaceutically acceptable compositions.

The outstanding properties are most effectively utilized when the conazole compound and the β-lactone compound are formulated into novel pharmaceutical composition with a pharmaceutically acceptable carrier according to conventional pharmaceutical compounding techniques.

In preparing the compositions in oral dosage form, the component drugs are intimately admixed with any of the usual pharmaceutical media, including for liquid preparations, liquid carriers such as water, glycols, oils, alcohols, and the like, and for solid preparations such as capsules and tablets, solid carriers such as starches, sugars, kaolin, ethyl cellulose, generally with a lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage. Compositions in unit dosage form constitutes an aspect of the present invention.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 200 to 400 milligrams of each of the component drugs.

The following examples illustrate novel compositions useful in the practice of the present invention, but are not to be construed as limiting:

EXAMPLE I 1000 compressed tablets each containing 200 milligrams of ketoconazole and 300 milligrams of β-lactone compound are prepared from the following formulation:

|  | Grams |
|---|---|
| Ketoconazole | 200 |
| β-Lactone compound | 300 |
| Starch | 750 |
| Dibasic calcium phosphate hydrous | 5000 |
| Calcium stearate | 2.5 |

The finely powered ingredients are mixed well and granulated with 10 percent starch paste. The granulation is dried and compressed into tablets.

EXAMPLE II 1000 hard gelatin capsules, each containing 210 milligrams of ketoconazole and 290 milligrams of β-lactone compound are prepared from the following formulation:

|  | Amount |
|---|---|
| Ketoconazole | 210 grams |
| β-Lactone compound | 290 grams |
| Starch | 250 grams |
| Lactose | 750 grams |
| Talc | 250 grams |
| Calcium stearate | 10 grams |

A uniform mixture of the ingredients is prepared by blending and used to fill two-piece hard gelatin capsules.

EXAMPLE III 250 milliliters of an injectable solution are prepared by conventional procedures having the following formulation:

|  | Amount |
|---|---|
| Dextrose | 12.5 grams |
| Water | 250 milliliters |

|  | Amount |
|---|---|
| Ketoconazole | 200 milligrams |
| β-Lactone compound | 200 milligrams |

The ingredients are blended and thereafter sterilized for use.

What is claimed is:

1. A synergistic antifungal composition suitable for treating mycotic infections in unit dosage form comprising a mycotic infection controlling amount in combination of:

(1) from about 200 to 400 milligrams of a 14α-methyl-demethylase inhibiting azole compound selected from the group consisting of (a) cis-1-acetyl-4-[4-[[2-(2,4-dichlorophenyl)-2-(1H-imidazol-1-yl-methyl)-1,3-dioxolan-4-yl]-methoxyl]phenyl]piperazine (ketoconazole), (b) α-(2,4-difluorophenyl)-α-(1H-1,2,4-triazol-1-yl-methyl)-1H-1,2-4-triazol-1-ethanol (fluconazole), (c) cis-4-[4-[4-[[2-(2,4-dichlorophenyl)-2-(1H-1,2,4-triazol-1-ylmethyl)-1,3-dioxolan-4-yl]-methoxy]-phenyl]1-piperazinyl]phenyl-2,4-dihydro-2-(1-methylpropyl)-3H-1,2,4-triazol-3-one (itraconazole) and (d) 1-[2,4-dichloro-β-(2,4-dichlorobenzyloxy)-phenethyl]imidazole nitrate (miconazole); and (2) from about 200 to 400 milligrams of a β-lactone compound having the formula

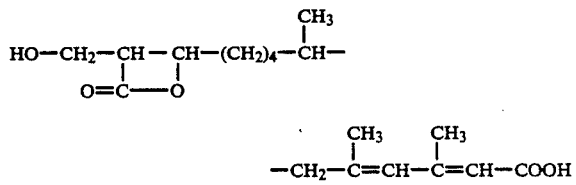

or a salt thereof
wherein said compounds are in admixture with a pharmaceutically acceptable carrier.

2. A composition according to claim 1 in which the azole compound is ketoconazole and the β-lactone compound is 11-(3-hydroxymethyl-4-oxo-2-oxetanyl)-7-methyl-2,4 undecadienoic acid or a salt thereof.

3. A composition according to claim 1 in which the unit dosage form is a tablet.

4. A composition according to claim 1 in which the unit dosage form is a capsule.

5. A parenteral pharmaceutical composition according to claim 1.

6. A composition according to claim 1 in which the azole compound is fluconazole and the β-lactone compound is 11-(3-hydroxymethyl-4-oxo-2-oxetanyl)-7-methyl-2,4-undecadienoic acid or a salt thereof.

7. A composition according to claim 1 in which the azole compound is itraconazole and the β-lactone compound is 11-(3-hydroxymethyl-4-oxo-2-oxetanyl)-7-methyl-2,4-undecadienoic acid or a salt thereof.

8. A fungicidal composition comprising in unit dosage form suitable for treating mycotic infections comprising a mycotic infection controlling amount in combination of:

(1) from about 200 to 400 milligrams of a compound having 14α-methyldemethylase inhibiting activity and named cis-1-acetyl-4-[4-[[2-(2,4-dichlorophenyl)-2-(1H-imidazole-1-ylmethyl)-1,3-dioxolan- 4-yl]-methoxyl]phenyl]piperazine (ketoconazole); and (2) from about 200 to 400 milligrams of a β-lactone compound and named 11-(3-hydroxymethyl-4-oxo-2-oxetanyl)-7-methyl-2,4-undecadienoic acid or a salt thereof.

9. A method for treating mycotic infections in a patient having such an infection comprising directing to the site in said patient where control is desired, a fungicidally effective amount of:

(1) a 14α-methyldemethylase inhibiting azole compound selected from the group consisting of (a) cis-1-acetyl-4-[4-[[2-(2,4-dichlorophenyl)-2-(1H-imidazol-1-yl-methyl)-1,3-dioxolan-4-yl]-methoxyl]phenyl]piperazine (ketoconazole), (b) α-(2,4-difluorophenyl)-α-(1H-1,2,4-triazol-1-yl-methyl)-1H-1,2,4-triazole-1-ethanol (fluconazole), (c) cis-4-[4-[4-[[2-(2,4-dichlorophenyl)-2-(1H-1,2,4-triazol-1-yl-methyl)-1,3-dioxolan-4-yl]-methoxy]-phenyl]-1-piperazinyl]phenyl-2,4-dihydro-2-(1-methylpropyl)-3H-1,2,4-triazol-3-one (itraconazole) and (d) 1-[2,4-dichloro-β-(2,4-dichlorobenzyloxy)phenethyl]imidazole nitrate (miconazole); and (2) from about 200 to 400 milligrams of a β-lactone compound having the formula

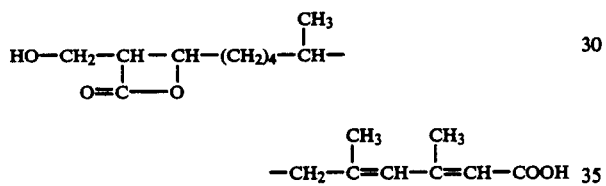

or a salt thereof
wherein the azole compound is employed in an amount of from about 2.85 to 4.75 mg/kg of body weight and the β-lactone compound or salt thereof is employed in an amount of from about 2.85 to 4.75 mg/kg of body weight.

10. A method according to claim 9 wherein the treatment is executed by the parenteral administration of said combination.

11. A method according to claim 9 wherein the treatment is by oral administration of said combination.

12. A method according to claim 9 wherein:
(1) the azole compound is cis-1-acetyl-4-[4-[[2-(2,4-dichlorophenyl)-2-(1H-imidazole-1-ylmethyl)-1,3-dioxolan-4-yl]methoxy]phenyl]piperazine (ketoconazole); and
(2) the β-lactone compound is 11-(3-hydroxymethyl-4-oxo-2-oxetanyl)-7-methyl-2,4-undecadienoic acid or a salt thereof.

13. A method according to claim 9 wherein:
(1) the azole compound is α-(2,4-difluorophenyl)-α-(1H-1,2,4-triazol-1-ylmethyl)-1H-1,2,4-triazole-1-ethanol (fluconazole); and
(2) the β-lactone compound is 11-(3-hydroxymethyl-4-oxo-2-oxetanyl)-7-methyl-2,4-undecadienoic acid or a salt thereof.

14. A method according to claim 9 wherein:
(1) the azole compound is cis-4-[4-[4-[[2-(2,4-dichlorophenyl)-2-(1H-1,2,4-triazol-1-ylmethyl)-1,3-dioxolan-4-yl]-methoxy]-phenyl]-1-piperazinyl]phenyl-2,4-dihydro-2-(1-methylpropyl)-3H-1,2,4-triazol-3-one (itraconazole); and
(2) the β-lactone compound is 11-(3-hydroxymethyl-4-oxo-2-oxetanyl)-7-methyl-2,4-undecadienoic acid or a salt thereof.

15. A method for killing fungi causing mycotic infections comprising administering to the site infected with fungi
(1) a β-lactone compound having the formula

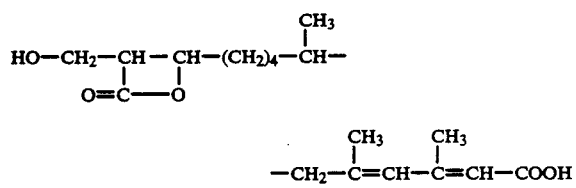

or a salt thereof, and
(2) cis-1-acetyl-4-[4-[[2-(2,4-dichlorophenyl)-2-(1H-imidazole-1-ylmethyl)-1,3-dioxolan-4-yl]methoxy]-phenyl]piperazine (ketoconazole),
wherein the β-lactone compound or salt thereof is employed in an amount of from about 2.85 to 4.75 mg/kg of body weight and ketoconazole is employed in an amount of from about 2.85 to 4.75 mg/kg of body weight.

* * * * *